United States Patent [19]  [11] Patent Number: 4,492,652
Kaplan  [45] Date of Patent: Jan. 8, 1985

[54] REACTIONS OF AROMATIC COMPOUNDS HAVING TWO OR MORE FUSED RINGS

[75] Inventor: Martin L. Kaplan, Morris Plains, N.J.

[73] Assignee: AT&T Laboratories, Murray Hill, N.J.

[21] Appl. No.: 462,405

[22] Filed: Jan. 31, 1983

Related U.S. Application Data

[63] Continuation of Ser. No. 104,159, Dec. 17, 1979, abandoned.

[51] Int. Cl.$^3$ .................... C07C 1/253; C07C 1/32
[52] U.S. Cl. ........................ 568/75; 260/429 AR; 549/15; 549/31; 549/234; 549/235; 423/440; 427/122; 427/228; 427/249; 427/255.6; 427/109; 568/18
[58] Field of Search ........... 427/122, 249, 228, 255.6, 427/109; 549/15, 234, 235, 31; 423/440; 260/139, 429 AR, 125

[56] References Cited

U.S. PATENT DOCUMENTS

| | | | |
|---|---|---|---|
| 3,017,286 | 1/1962 | Kane et al. ..................... | 423/440 |
| 3,086,001 | 4/1963 | Wildi ............................. | 260/125 |
| 3,162,641 | 12/1964 | Acker et al. ................. | 260/326.9 X |
| 3,269,802 | 8/1966 | Wainer et al. ............... | 423/440 X |
| 3,642,522 | 2/1972 | Gass et al. .................... | 427/249 |
| 3,848,062 | 11/1974 | Steiger et al. ................ | 423/440 |
| 3,912,832 | 10/1975 | Araki et al. .................. | 427/249 X |
| 3,940,509 | 2/1976 | Youtsey et al. .............. | 427/288 X |
| 3,949,106 | 4/1976 | Araki et al. .................. | 427/249 |
| 3,982,100 | 9/1976 | Hevert ......................... | 427/249 X |
| 3,995,143 | 11/1976 | Hevert ......................... | 427/249 X |
| 4,018,943 | 4/1977 | Youtsey et al. .............. | 427/122 X |

OTHER PUBLICATIONS

Whitmore; "Organic Chemistry", (1937), p. 864, D. Van Nostrand Co., Inc., N.Y., N.Y.
Isaacs; "Reactive Intermediates in Organic Chemistry", (1974), pp. 294-296, John Wiley & Sons, N.Y.
Weygand-Hilgetag; Preparative Organic Chemistry", (1972), pp. 894-903, John Wiley & Sons, N.Y.
Fields; J. Org. Chem., 31, (1966), pp. 3307-3309.
Torrance; Accounts of Chemical Research, 12, (1979), pp. 79-86.
Brown; "Pyralytic Methods in Organic Chemistry", (1980), pp. 57, 186, 187, 190, 191, Academic Press, N.Y.
Hawley; "The Condensed Chemical Dictionary", 9th ed., p. 735 (1975), Van Nostrand, N.Y.
Weygand; Organic Preparations, (1945), pp. 348-351, Interscience, N.Y.
Walker, Jr.; Chemistry and Physics of Carbon; vol. 7, (1971), pp. 237-376; Marcel Dekker, Inc., N.Y.

Primary Examiner—Joseph P. Brust
Attorney, Agent, or Firm—Bruce S. Schneider

[57] ABSTRACT

The pyrolysis of aromatic compounds with fused rings in the aromatic system which form free radicals on the peri position, for example, by eliminating a stable inorganic gas produces desirable products. These products include electrically conductive inert films. Further, with the addition of suitable inorganic compounds to the reactant, superconducting materials are obtainable. The addition of sulfur to the pyrolysis reactant also is possible and allows production of compounds useful as donors for the production of organic electrically conducting compositions.

8 Claims, 2 Drawing Figures

REACTIONS OF AROMATIC COMPOUNDS HAVING TWO OR MORE FUSED RINGS

This is a continuation of application Ser. No. 104,159 filed Dec. 17, 1979, now abandoned.

BACKGROUND OF THE INVENTION

1. Field of the Invention

This invention relates to organic chemical synthesis and, more particularly, to processes involving aromatic compounds.

2. Art Background

Conductive carbon compositions such as graphite play an extremely important role in industrial products and processes. Because of its significant mechanical and electrical properties, graphite is extensively utilized. For this reason, research on the production of graphite, or compounds with the electrical or mechanical properties of graphite, has been intensive. For example, a plethora of organic compounds has been pyrolyzed in an attempt to produce carbon compositions with useful properties, e.g., high conductivity. (See E. Fitzer et al, *The Chemistry and Physics of Carbon*, 7, 237 (1971) for a review of this work.)

The interest in electrical properties such as found in graphite has also spurred research concerning organic conductors. These organic compounds conduct through an ionic crystal composed of organic anions and cations. Organic conductors such as tetrathiafulvalenium-tetracyanoquinodimethanide have shown promising conductivities, i.e., conductivities approaching $10^3$ ohm$^{-1}$cm$^{-1}$.

SUMMARY OF THE INVENTION

By pyrolysis of appropriately chosen aromatic compounds, materials having good electrical properties, e.g., relatively high conductivity are producible. The appropriate aromatic compounds are those having fused rings which, when heated, produce free radicals on adjacent peri positions of the aromatic compound by, for example, eliminating a stable inorganic gas from these positions. (For the purposes of this application, carbon oxides such as carbon monoxide and carbon dioxide are considered inorganic gases.) When a heated object is placed in the effluent from this pyrolysis reaction, it is coated by a conductive film. This film, although analyzed as essentially entirely carbon (i.e., >99%), has an x-ray crystallographic diffraction behavior which is not indicative of a graphitic structure. In fact, d-spacings obtained by electron diffraction resemble those of diamond. The films, nevertheless, have high relative conductivity, e.g., 250 ohm$^{-1}$cm$^{-1}$, are extremely adherent to materials such as ceramics, glass and metals, e.g., tantalum, and are inert to most corrosive compounds. Thus, the films are useful both as an electrical conductor, for example, as a conducting film on an optical fibre, or as a film protection against corrosion. Additionally, when this pyrolysis is performed in the presence of an added material such as sulfur, compounds containing the added material that are useful as constituents in organic conductors are produced.

The properties of the pyrolytically produced materials are also modifiable by including an appropriate additive with the initial reactant. For example, a superconducting material having a critical temperature of about 12 degrees K. is produced when niobium pentachloride is included during the pyrolysis of 3, 4, 9, 10-perylenetetracarboxylic dianhydride.

DETAILED DESCRIPTION

Figure 1:
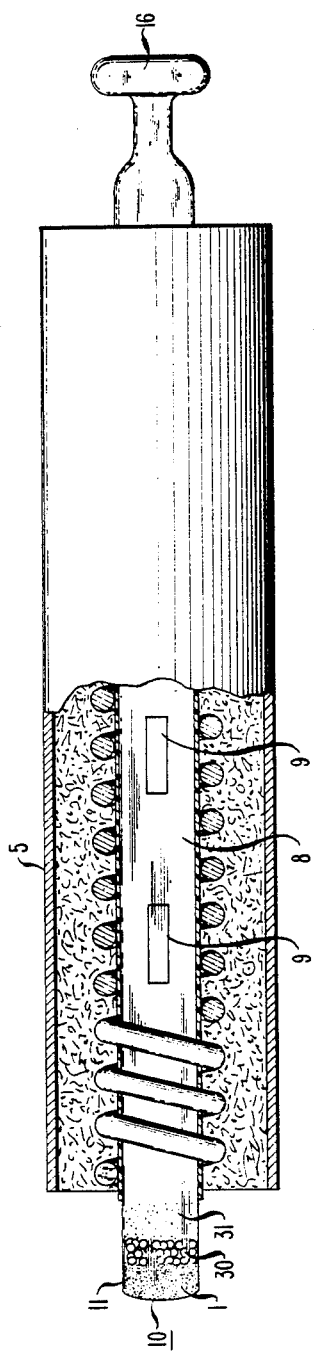
FIG. 1 is a schematic illustration of an apparatus useful for practicing the subject invention.

Techniques for the pyrolysis of organic compounds are well known. Although the subject invention is not limited to any one particular technique, in a peferred embodiment, an apparatus shown in FIG. 1 is utilized. The organic compound to be pyrolyzed, 1, (FIG. 1), is placed in reaction tube, 10. For convenience, to maintain the reactant in the desired position a layer of porcelain rings, 30, and a layer of quartz wool, 31, are also inserted into the tube after the reactant. The articles to be coated, 9, with the product of the pyrolysis reaction are placed in the reaction tube downstream from the reactants. Reaction tube, 10, is placed in tube furnace, 5, with the tube section, 11, outside the furnace. After the furnace has been heated to the pyrolysis temperature, the tube is moved so that section, 11, approaches the inside of the furnace and this movement is continued until the reactant is inside the furnace. The reaction temperature utilized should be equal to or exceed the decomposition temperature of the organic compound reactant. Typically, this temperature is in the range 700 degrees C. to 900 degrees C. Temperatures greater than 1200 degrees C. are not desirable, since common containers such as quartz begin to soften, and temperatures below 700 degrees C. are usually inadequate to induce decomposition.

Figure 2:
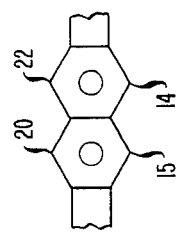
FIG. 2 is a represenatation useful in defining appropriate reactants.

The organic compound to be pyrolyzed should be an aromatic compound having a nucleus containing fused aromatic rings where the aromatic nucleus is arranged to have peri positions. Additionally, upon pyrolysis, these compounds should undergo a change to produce free radicals at the peri positions, i.e., producing a free radical at positions 20 and 22 and/or 15 and 14 (FIG. 2), e.g., by eliminating an inorganic gas from adjacent peri positions, i.e., from the positions marked 20 and 22 and/or the positions marked 15 and 14 in FIG. 2. For example, when 3, 4, 9, 10-perylenetetracarboxylic dianhydride is pyrolyzed CO and $CO_2$ are eliminated to at least initially yield a free radical involving the peri position, e.g.,

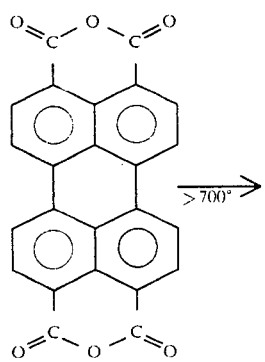

-continued $CO_2 + CO +$ 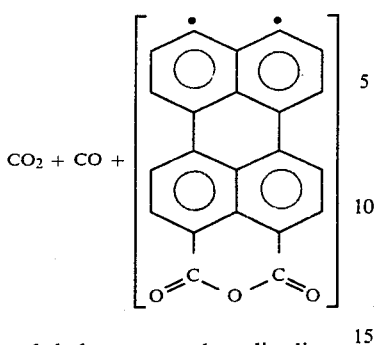

Similarly, 1, 4, 5, 8-naphthalenetetracarboxylic dianhydride

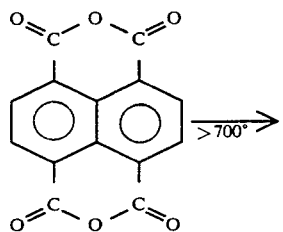 $\xrightarrow{>700°}$ $CO + CO_2 +$ 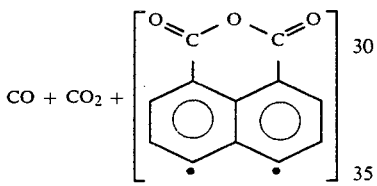

eliminates CO and $CO_2$ to at least initially yield reactive radicals such as those shown. Although the exact nature of the total reaction processes is unknown the diradical is illustrative of radical intermediates generated during the various pyrolysis reactions.

The pyrolysis reaction produces a low volatility product and a set of products with a higher volatility. To condense the low volatility product the object to be coated must also be heated. An adherent film of the low volatility product does not form on room temperature articles. Typically, temperatures are employed which are approximately the same as the temperature used for pyrolysis. It is also possible to employ temperatures slightly less than the pyrolysis temperature. However, generally the temperature employed should be within 100 degrees C. of the pyrolysis temperature. A convenient method of heating the articles to be coated, 9, to an appropriate temperature is to place the articles at a position, 8, so that they are inside the heating area of the oven. Naturally, to achieve a substantially uniform coating, all surfaces of the body, 9, to be coated should be accessible to the decomposition effluent. After the effluent has passed over the articles to be coated, it is vented through port, 16. (It should be noted that this effluent contains the products with higher volatility.)

It is possible to collect the more volatile decomposition products by allowing condensation on the reaction tube or other surface outside the heating area before the effluent is vented. For example, if sulfur is mixed with the aromatic compounds used as reactants, the sulfur is incorporated into the compounds to form a higher volatility product having the reactant ring structure plus an additional sulfur-containing ring. For example, compounds such as 1, 4, 5, 8-naphthalenetetracarboxylic dianhydride are mixed with reactants such as sulfur and heated to the temperatures as described previously. The sulfur adds to the aromatic compounds at the points where the gaseous precursor of the compound is expelled to produce compounds such as 1, 4, 5, 8-tetrathianaphthalene.

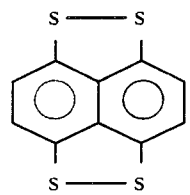

The more volatile products obtained by this process are useful for applications such as the production of organic compounds that are electrically conducting. To produce a conducting salt, the more volatile product of the subject sulfur addition process is mixed with an appropriate electron acceptor such as TCNQ. (See U.S. Pat. No. 3,162,641 for a description of TCNQ and Torrance, J., *Accounts of Chemical Research*, 12, 79, (1979) for a method of making organic conducting salts.) The lower volatility products when sulfur is added are deposited as described previously and has similar electrical and mechanical properties to films obtained when no sulfur is added.

Additionally, it is possible to change the electrical properties of the low volatility product film by adding compounds to the reactants. For example, it is possible to add a niobium compound such as niobium pentachloride to the reactant aromatic compound to produce low volatility product films which exhibit superconductive properties at temperatures of about 12 degrees K. The reaction temperatures utilized are those described above.

The following examples are illustrative of the subject process and products:

EXAMPLE 1

Approximately 0.25 gram of 1, 4, 5, 8-naphthalenetetracarboxylic dianhydride (purer than 99%) was pyrolyzed. This pyrolysis was accomplished by using the apparatus illustrated in FIG. 1. In this respect, the dianhydride, 1, was placed in the tube. Porcelain rings, 30, and quartz wool, 31, were sequentially placed in the tube to hold the dianhydride in position and to allow sufficient transfer of heat. Three quartz plates measuring approximately 7 cm × 1½ cm × 1.5 mm thick were placed at position, 8, in the tube. The tube containing the dianhydride was placed so that the dianhydride remained outside the heating zone of tube furnace, 5, at room temperature. The tube was then evacuated to a pressure of less than $10^{-2}$ Torr. The furnace was then heated to a temperature of about 900 degrees C. When this temperature was achieved, the tube was moved so that the portion of the tube containing the dianhydride was gradually brought into the heating area. This movement of the tube was controlled so that the pressure produced by the onset of decomposition of the dianhydride did not exceed 0.3 Torr. Although this step was not critical, for experimental covenience this gradual decomposition was utilized. It was, however, noted that films having a smoother surface were produced when the decomposition rate was controlled.

After the pressure in the system had dropped to its initial reading before decomposition was induced, the tube was removed. The tube was then allowed to cool to room temperature. The glass slides were removed and these slides were essentially uniformly coated with a lustrous metallic appearing mirror surface. In addition, it was noted that the tube was also coated with a similar material. The films obtained were generally in the thickness range of 0.3 to 1μ. For these films, ohmmeter measurements indicated a conductivity of approximately 100 ohms$^{-1}$cm$^{-1}$.

EXAMPLE 2

The procedure of Example 1 was followed except that the material used as the reactant was 3, 4, 9, 10-perylenetetracarboxylic dianhydride. Additionally, pyrolysis was performed at both 700 and 800 degrees C. The samples obtained for the procedure using 800 and 900 degrees C. temperatures produced similar results. However, the sample pyrolyzed at a temperature of 700 degrees C. produced diminished quantities of the desired conductive films.

EXAMPLE 3

Approximately 5 grams of sulfur and 1 grams of 1, 4, 5, 8-naphthalenetetracarboxylic dianhydride was placed in the reactant tube as described in Example 1. The procedures as described in Example 1 were followed. Temperatures at both approximately 800 and 900 degrees C. were utilized. The quartz plates for both temperatures were coated with a film having essentially the same properties as described in Example 1. However, x-ray fluorescence measurements indicated that the material on these quartz plates contained chemically bound sulfur. Additionally, material condensed on the reaction tube in the area outside the tube furnace downstream from the reactant. This material was scraped off the tube and its constituent parts separated using silica gel thick layer chromotography. Three fractions appeared. One was characterized as unreacted sulfur, the second was characterized as 1, 5, 4, 8-tetrathianaphthalene by IR spectroscopy, and the third as 1, 8-dithianaphthalene also by spectroscopy.

EXAMPLE 4

The tube was filled as described in Example 1 with 100 mg of 3, 4, 9, 10-perylenetetracarboxylic dianhydride and 0.25 gram of niobium pentachloride. The tube was inserted into the tube furnace with the material outside the heating zone. A vacuum system was attached to the tube, but not activated. The furnace was then heated to 900 degrees C. After the tube reached this temperature, the vacuum system was activated and the tube slowly pulled into the heating zone as described in Example 1. (This procedure was followed because of the high volatility of niobium pentachloride.) X-ray fluorescence measurements of the films indicate that no chlorine had been incorporated into the film. Additionally, electron diffraction measurements indicated that niobium carbide was present in the film. Conductivity measurements done at various temperatures indicated a superconductivity onset ($T_c$) at approximately 12 degrees K.

I claim:

1. A process for the production of a carbon containing body comprising the steps of pyrolyzing a carbon containing compound and collecting a reaction product from said pyrolysis characterized in that said carbon containing compound comprises an aromatic organic compound having fused aromatic rings which are pyrolyzed at a temperature in the range from 700 to 1200 degrees C., and which due to said pyrolysis, forms free radicals at the peri positions of said fused rings of said carbon containing compound, wherein said free radicals are formed due to said pyrolysis through the production of a stable inorganic gas by removal of a substituent from said peri positions of said compound without the destruction of said fused aromatic rings, wherein said pyrolysis is performed in the absence of an additional agent which reacts with said free radicals and wherein said reaction product is deposited on a substrate which is heated to a temperature below said pyrolysis temperature sufficient to allow said deposition.

2. The process of claim 1 wherein said carbon containing compound is 3, 4, 9, 10-perylenetetracarboxylic dianhydride.

3. A product formed by the process comprising the steps of pyrolyzing a carbon containing compound and collecting a reaction product from said pyrolysis characterized in that said carbon containing compound comprises an aromatic organic compound having fused aromatic rings which, due to said pyrolysis at a temperature in the range from 700 to 1200 degrees C., forms free radicals at the peri positions of said fused rings of said carbon containing compound, wherein said free radicals are formed due to said pyrolysis through the production of a stable inorganic gas by removal of a substituent from said peri positions of said compound without the destruction of said fused aromatic rings, wherein said pyrolysis is performed in the absence of an additional agent which reacts with said free radicals and wherein said reaction product is deposited on a substrate which is heated to a temperature below said pyrolysis temperature sufficient to allow said deposition.

4. The product of claim 3 wherein said free radicals are formed by elimination of a stable inorganic gas.

5. A process for the production of a carbon containing body comprising the steps of pyrolyzing a carbon containing compound and collecting a reaction product from said pyrolysis characterized in that said carbon containing compound comprises an aromatic organic compound having fused aromatic rings which, due to said pyrolysis at a temperature in the range from 700 to 1200 degrees C., forms free radicals at the peri positions of said fused rings of said carbon containing compound, wherein said free radicals are formed due to said pyrolysis through the production of a stable inorganic gas by removal of a substituent from said peri positions of said compound without the destruction of said fused aromatic rings, wherein sulfur is the only agent present during said pyrolysis step which reacts with said radicals, and wherein said collected reaction product is a high volatility product.

6. The process of claim 5 wherein said compound is 3,4,9,10-perylenetetracarboxylic dianhydride.

7. The process of claim 5 wherein said free radicals are formed by elimination of a stable inorganic gas.

8. A process for the production of a carbon containing body comprising the steps of pyrolyzing a carbon containing compound and collecting a reaction product from said pyrolysis characterized in that said carbon containing compound comprises an aromatic organic compound having fused aromatic rings which, due to said pyrolysis at a temperature in the range from 700 to 1200 degrees C., forms free radicals at the peri positions of said fused rings of said carbon containing compound, wherein said free radicals are formed due to said pyrolysis through the production of a stable inorganic gas by removal of a substituent from said peri positions of said compound without the destruction of said fused aromatic rings, and wherein a niobium compound is the only agent present during said pyrolysis step which reacts with said radicals.

* * * * *